(12) United States Patent
Farcet

(10) Patent No.: US 7,816,464 B2
(45) Date of Patent: Oct. 19, 2010

(54) POLYMER PARTICLE DISPERSION, COSMETIC COMPOSITION COMPRISING IT AND COSMETIC PROCESS USING IT

(75) Inventor: Céline Farcet, Paris (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 12/453,169

(22) Filed: Apr. 30, 2009

(65) Prior Publication Data

US 2009/0214461 A1 Aug. 27, 2009

Related U.S. Application Data

(63) Continuation of application No. 11/353,981, filed on Feb. 15, 2006, now Pat. No. 7,585,922.

(60) Provisional application No. 60/661,001, filed on Mar. 14, 2005.

(30) Foreign Application Priority Data

Feb. 15, 2005 (FR) .................................. 05 50430

(51) Int. Cl.
C08L 83/00 (2006.01)
A61K 8/00 (2006.01)
B32B 9/04 (2006.01)

(52) U.S. Cl. .......................... 525/477; 424/59; 424/401

(58) Field of Classification Search .................. 424/401
See application file for complete search history.

(56) References Cited

U.S. PATENT DOCUMENTS

| | | | |
|---|---|---|---|
| 4,584,356 A | 4/1986 | Crivello |
| 4,689,289 A | 8/1987 | Crivello |
| 5,162,396 A | 11/1992 | Hilty et al. |
| 5,171,809 A | 12/1992 | Hilty et al. |
| 5,219,560 A | 6/1993 | Suzuki et al. |
| 5,523,365 A | 6/1996 | Geck et al. |
| 5,618,524 A | 4/1997 | Bolich et al. |
| 5,625,005 A | 4/1997 | Mallya et al. |
| 5,658,557 A | 8/1997 | Bolich et al. |
| 5,736,125 A | 4/1998 | Morawsky et al. |
| 5,753,216 A | 5/1998 | Leitch et al. |
| 5,780,553 A | 7/1998 | DeSimone et al. |
| 5,804,173 A | 9/1998 | Hutchins et al. |
| 5,851,517 A | 12/1998 | Mougin et al. |
| 5,945,095 A | 8/1999 | Mougin et al. |
| 5,965,115 A | 10/1999 | Bolich et al. |
| 5,968,495 A | 10/1999 | Bolich et al. |
| 5,972,356 A | 10/1999 | Peffly et al. |
| 5,985,294 A | 11/1999 | Peffly |
| 5,985,295 A | 11/1999 | Peffly |
| 5,997,853 A | 12/1999 | Bolich et al. |
| 6,177,063 B1 | 1/2001 | Hutchins |
| 6,254,876 B1 | 7/2001 | de la Poterie et al. |
| 6,254,877 B1 | 7/2001 | De La Poterie et al. |
| 6,280,748 B1 | 8/2001 | Morita et al. |
| 6,326,013 B1 | 12/2001 | Lemann et al. |
| 6,361,782 B1 | 3/2002 | Chevalier et al. |
| 6,365,672 B1 | 4/2002 | Adams et al. |
| 6,403,106 B1 | 6/2002 | Sebag et al. |
| 6,432,418 B1 | 8/2002 | Dubief et al. |
| 6,464,969 B2 | 10/2002 | De La Poterie et al. |
| 6,548,132 B1 | 4/2003 | Clarke et al. |
| 6,565,839 B2 | 5/2003 | de la Poterie et al. |
| 6,685,925 B2 | 2/2004 | Hajduk et al. |
| 6,989,417 B2 | 1/2006 | Bitler et al. |
| 2001/0018484 A1 | 8/2001 | Bitler et al. |
| 2002/0098214 A1 | 7/2002 | Adams et al. |
| 2003/0232028 A1 | 12/2003 | Loffler et al. |
| 2003/0235548 A1 | 12/2003 | Lu |
| 2004/0013615 A1 | 1/2004 | Dubief et al. |
| 2004/0146473 A1 | 7/2004 | Lion |
| 2004/0156804 A1 | 8/2004 | Poterie et al. |
| 2004/0156812 A1 | 8/2004 | Lion |

FOREIGN PATENT DOCUMENTS

| | | |
|---|---|---|
| EP | 0 096 459 A2 | 12/1983 |
| EP | 0 749 747 B1 | 12/1998 |
| EP | 0 895 467 B1 | 2/1999 |
| EP | 0 963 751 B1 | 12/1999 |
| EP | 1 347 013 A2 | 9/2003 |
| EP | 1 428 843 A1 | 6/2004 |
| WO | WO 01/77198 A1 | 10/2001 |
| WO | WO 2004/055077 A2 | 7/2004 |
| WO | WO 2004/055081 A2 | 7/2004 |

OTHER PUBLICATIONS

French Search Report for FR 05 50430, dated Nov. 15, 2005.

(Continued)

*Primary Examiner*—Randy Gulakowski
*Assistant Examiner*—Robert Loewe
(74) *Attorney, Agent, or Firm*—Finnegan, Henderson, Farabow, Garrett & Dunner, L.L.P.

(57) ABSTRACT

The present disclosure relates to a cosmetic composition comprising, in a cosmetically acceptable medium, at least one dispersion of polymer particles in a liquid silicone medium, the polymer being a copolymer comprising at least one first block that is soluble and at least one second block that is insoluble in the silicone medium.

Another aspect of the present disclosure relates to a dispersion of polymer particles in a liquid silicone medium, and also to a cosmetic process for making up, cleansing, protecting against the sun, shaping, dyeing or caring for keratin materials, such as the body or facial skin, the nails, the hair and/or the eyelashes, and for use with the present composition.

1 Claim, No Drawings

OTHER PUBLICATIONS

Eric A. Grulke, "Solubility Parameter Values," Polymer Handbook, Third Edition, John Wiley & Sons, pp. 519-559 (1989).

"Graft Copolymers With Short Side Chains," Polymer Letters, Part B, vol. 5, No. 6, pp. 477-481 (1967).

Hansen, "Three Dimensional Solubility Parameters—Key to Paint Component Affinities," Journal of Paint Technology, vol. 39, No. 505, pp. 105-113 (1967).

Database WPI, Section Ch, Week 200456, Derwent Publications Ltd., London, GB; AN 2004-573565, XP002386588.

European Search Report for EP 06 29 0132, dated Jun. 26, 2006.

POLYMER PARTICLE DISPERSION, COSMETIC COMPOSITION COMPRISING IT AND COSMETIC PROCESS USING IT

This is a continuation of application Ser. No. 11/353,981, filed Feb. 15, 2006 now U.S. Pat. No. 7,585,922, which claims the benefit of French Patent Application No. 05 50430, filed Feb. 15, 2005, and U.S. Provisional Application No. 60/661, 001, filed Mar. 14, 2005, all of which are incorporated herein by reference.

This application claims benefit of U.S. Provisional Application No. 60/661,011, filed Mar. 14, 2005, the contents of which are incorporated herein by reference. This application also claims benefit of priority under 35 U.S.C. §119 to French Patent Application No. FR 05 50430, filed Feb. 15, 2005, the contents of which are also incorporated herein by reference.

The present disclosure relates to novel polymer particle dispersions and to their use in cosmetics; the disclosure also relates to compositions, for example cosmetic compositions, comprising these dispersions.

It is known practice to use in cosmetics dispersions of polymer particles, generally of nanometric size, in organic media.

Thus, European Patent Application No. EP-A-0 749 747 describes a cosmetic composition comprising a polymer particle dispersion, in a non-aqueous medium, the dispersion being stabilized by adding stabilizing polymers, which bind non-covalently by means of physical interactions on the polymer particles. However, this type of composition has the following drawbacks: it requires the addition to the non-aqueous medium of a larger amount of stabilizing polymers than that effectively bound to the insoluble polymer particles, in order to obtain a relatively stable dispersion of the particles. During the addition of adjuvants such as pigments to the compositions, some of the stabilizing polymers may have a tendency to become desorbed from the insoluble polymer particles and to combine with the adjuvants, which contributes towards destabilizing the dispersion, such as by formation of aggregates between the polymer particles.

Cosmetic compositions comprising dispersions, in a silicone medium, of acrylic polymer particles comprising a skeleton that is insoluble in the medium, and a part that is soluble in the medium, consisting of side chains covalently bonded to the skeleton, are also known, from European Patent Application No. EP 1 428 843. In this case, the polymer particles are stabilized with a polymer (macromer) that is chemically bonded to the polymer particles.

In both cases, the nature of the stabilizing polymer is not easily modified, whether in terms of chemical nature, molar mass and/or architecture, and requires a specific synthesis. Moreover, it is not easy to modify the properties of the particle core, whether in terms of molecular mass and/or architecture.

The present inventor has discovered, surprisingly, novel polymer particle dispersions that may afford good cosmetic properties such as good adhesion to the support (such as skin or hair) and thus good staying power of the cosmetic composition.

Moreover, since the dispersion according to the disclosure does not comprise any stabilizer within the meaning of the prior art, the presently disclosed dispersion may be more stable over time than the usual dispersions, which may lead to better stability of the composition comprising it and easier formulation.

Finally, the comfort of the composition may be improved.

One aspect of the present disclosure is a cosmetic composition comprising, in a cosmetically acceptable medium, at least one dispersion of polymer particles in a liquid silicone medium, the polymer being a copolymer comprising at least one first block that is soluble in the silicone medium and at least one second block that is insoluble in the silicone medium.

As disclosed herein, it may be possible to modify the physicochemical properties of the dispersion, and thus of the composition comprising it, by appropriately selecting the monomers and the silicone medium of which it is composed. This possibility was not foreseeable with the prior art, and makes it possible, for example, to obtain a dispersion that has a great affinity for the oily silicone media usually used in cosmetics; and also makes it possible to prepare a dispersion whose deposit does not have any tacky nature.

Micelles of block copolymer, for instance in carbon-based organic medium, are known in general. Mention may be made, for example, of Patent Application No. WO 01/77198 relating to a process for preparing microgels by RAFT polymerization in the presence of a chain-transfer agent, which comprises preparing a block copolymer comprising solvophobic monomers and solvophilic monomers, and then in dispersing the block copolymer in a dispersion medium to form micelles, which will be stabilized to give the expected microgel. In WO 01/77198, the dispersion medium may be organic carbon-based, aqueous or aqueous-organic.

However, it is not envisaged in WO 01/77198 to use per se the micelles thus prepared; they serve to form microgels by crosslinking, the microgels allowing pigments or dyes to be encapsulated, for example, and being able to be used in various fields such as industrial coating. The crosslinked microgels thus obtained do not make it possible to obtain deposits that are, for example, film-forming, with good staying power and that are easy to remove. However, at least one of these properties may be achieved by one or more aspects of the invention disclosed herein.

Moreover, WO 01/77198 does not in any way mention the possibility of preparing a particle dispersion in silicone media.

In certain fields of cosmetics, for example makeup, the compositions generally comprise silicone fatty substances, such as silicone oils and/or silicone waxes; traditionally, the introduction of polymer particles, dispersed in hydrocarbon-based oils, into these compositions is relatively difficult, and may prove to be almost impossible when the amount of silicone oil is excessive due to the loss of stability of the composition. Silicone oils provide good cosmetic properties, such as a soft feel, good slipperiness of the composition and less of a greasy effect. Therefore, it is not desirable to dispense with them.

The present disclosure addresses the problem of the introduction of polymer particles into compositions containing silicone fatty substances by proposing dispersions of polymer particles in a silicone medium, which allow the incorporation of a large amount of polymer particles into silicone-based cosmetic compositions while also allowing the compositions to retain good stability.

The polymer particle dispersion according to the present disclosure thus comprises a copolymer that comprises at least one first block that is soluble in the silicone medium and at least one second block that is insoluble in the silicone medium.

In the present disclosure, the term "block" means a polymer sequence formed from several monomers, such as from at least 5 monomers, which may be identical or different, and which may thus be in the form of a random, alternating, gradient and block, such as diblock, triblock or multiblock, and homopolymer or copolymer.

For instance, the block may be of homopolymer or gradient type.

For each block, the choice of monomers and of their amount, and also of the architecture of the block, may be made by a person skilled in the art on the basis of his general knowledge so as finally to obtain a block having the required solubility (soluble or insoluble) in the silicone medium under consideration.

In at least one embodiment the copolymer finally obtained is the "diblock" type, i.e. it comprises only two blocks, one being soluble in the medium, the other being insoluble therein. In other embodiments, the final copolymer may be of the "triblock" or even "multiblock" (more than three blocks) type.

In at least one embodiment, the sequence of the soluble and insoluble blocks is alternating. Each soluble block may be of identical or different length and/or molar mass, of identical or different chemical nature, and of identical or different architecture. Each insoluble block may be of identical or different length or molar mass, of identical or different chemical nature, and of identical or different architecture.

In at least one embodiment, the copolymer according to the disclosure is linear; however, it may also be branched and/or grafted.

In at least one embodiment, the copolymer according to the present disclosure is not crosslinked; however, it may be crosslinked by adding a crosslinking agent; for example the crosslinked block may be the insoluble block, which means that the final particles may have a crosslinked core.

The term "soluble" as used herein means that the block is fully dissolved (without any apparent deposit, or insoluble aggregate or sediment), visually, at 20° C., at a concentration of greater than or equal to 5% by weight, in the silicone medium under consideration.

The dispersions according to the present disclosure may also be in the form of polymer micelles (or particles) as a stable dispersion in the medium under consideration. These micelles (or particles) may range in size from 5 to 1000 nm, for instance from 10 to 500 nm, such as 20 to 300 nm and further for example from 30 to 200 nm in size, which allows great stability of the dispersion over time to be obtained.

The term "polymer micelles," as used herein, means self-dispersed particles obtained by self-assembly of the copolymers as defined below.

Thus, it may be considered that the polymerization of the monomer(s) of which the first block was composed, of initiator and/or of control agent leads to a first block that may be soluble in the medium under consideration. The addition of the monomer(s) intended to compose the core of the particle leads to the formation of the copolymer, such as a block copolymer, of soluble or insoluble type, this copolymer becoming spontaneously organized into a polymer micelle, i.e. forming a self-dispersed polymer particle in silicone medium.

One of the advantages associated with the present disclosure is that it is possible in a single step to form dispersed copolymer particles, of which the characteristics of the soluble part and those of the core of the particle may be simultaneously controllable.

The copolymers according to the present disclosure for instance have a number-average molecular weight (Mn) ranging from 1000 to 700 000, such as from 10 000 to 500 000 and further for example from 15 000 to 350 000, or from 30 000 to 150 000.

In at least one embodiment, the copolymer according to the present disclosure has a mass polydispersity index (Ip) of less than or equal to 6, for instance ranging from 1.05 to 4 and further from 1.1 to 3 or from 1.15 to 2.5.

The mass polydispersity index (Ip) of the copolymer may be equal to the ratio of the weight-average molecular mass (Mw) to the number-average molecular mass (Mn). A low mass polydispersity reflects approximately identical chain lengths.

The weight-average (Mw) and number-average (Mn) molecular masses are determined by gel permeation liquid chromatography (GPC), eluted with THF, on a calibration curve established with linear polystyrene standards, using a refractometric detector.

For instance, the dispersion according to at least one embodiment of the disclosure may have a uniform particle size polydispersity, which means that all the particles are of the same size; e.g., the dispersion may be such that at least 50% in numerical terms of the particles of the dispersion have an identical or virtually identical diameter (difference of less than 10%); this contributes towards better stability of the dispersion over time (i.e., no decantation, flocculation and/or sedimentation).

This is an advantage over certain dispersions found in the carbon-based medium of the prior art, prepared according to "conventional" free-radical polymerization processes. This may be explained by the fact that in these processes, the product obtained has a heterogeneous chemical composition since it is generally a mixture of homopolymers and copolymers.

In the present disclosure, the vast majority or even all of the chains (depending on the chosen polymerization technique) may be in the form of block copolymer, which may improve the stability of the dispersions in the compositions. Moreover, the copolymers according to the present disclosure may have narrow molar mass and chemical composition distributions and controlled molar masses, which may also make it possible to control the size of the particles and their size distribution.

The copolymer according to the present disclosure may thus comprise a first block that is soluble in the silicone dispersion medium and at least one second block that is insoluble in the medium.

The soluble block may comprise 50% to 100% by weight of monomer(s) that is (are) soluble in the medium, such as from 60% to 90% by weight and further still from 70% to 80% by weight of soluble monomer(s), alone or as a mixture. However, the soluble block may also comprise from 0% to 50% by weight, such as from 10% to 40% by weight and further still from 20% to 30% by weight of monomer(s) that is (are) insoluble in the medium, alone or as a mixture.

Similarly, the insoluble block may comprise 50% to 100% by weight of monomer(s) that is (are) insoluble in the medium, such as from 60% to 90% by weight and further still from 70% to 80% by weight of insoluble monomer(s), alone or as a mixture. However, the insoluble block may also comprise 0% to 50% by weight, such as from 10% to 40% by weight and further for example from 20% to 30% by weight of monomer(s) that is (are) soluble in the medium, alone or as a mixture.

A person skilled in the art will know how to select, on the basis of his general knowledge, the soluble and insoluble monomer(s), and also the amounts thereof, in order finally to obtain a block having the desired solubility (soluble or insoluble) in the silicone medium under consideration.

As used herein, the term "monomer that is soluble in the medium" means any monomer whose homopolymer is in soluble form, i.e. fully dissolved at a concentration of greater than or equal to 5% by weight at room temperature (20° C.), in the medium.

As used herein, the term "insoluble monomer" means any monomer whose homopolymer is not in soluble form, i.e. not fully dissolved at a concentration of greater than or equal to 5% by weight at room temperature (20° C.), in the medium. However, the insoluble monomers may, as monomers, be soluble in the medium under consideration, given that they become insoluble after polymerization.

In any case, the proportion of soluble block and of insoluble block in the copolymer should be such that the copolymer can form a polymer micelle.

In at least one embodiment, the insoluble block(s) may represent(s) 15% to 97% by weight, such as from 30% to 95% by weight, even further such as from 50% to 93% by weight, for example from 60% to 92% by weight and further still from 75% to 90% by weight, relative to the total weight of the copolymer.

In at least one embodiment, the soluble block(s) may represent(s) 3% to 85% by weight, such as from 5% to 70% by weight, further such as from 7% to 50% by weight, such as from 8% to 40% by weight and further still from 10% to 25% by weight relative to the total weight of the copolymer.

As soluble monomers that may be used, non-limiting mention may be made, alone or as a mixture, of the following monomers:

ethylenic monomers in which the ester group contains silanes, silsesquioxanes, siloxanes or carbosiloxane dendrimers as described in European Patent No. EP 963 751, with the exception of monomers containing only one silicon atom such as methacryloxypropyltrimethoxysilane. In at least one embodiment, the ethylenic monomers are chosen from (meth)acryloxypropyltris(trimethylsiloxy)silane, (meth)acryloxypropylbis(trimethylsiloxy)methylsilane, (meth)acryloxymethyltris(trimethylsiloxy)silane and (meth)acryloxymethylbis(trimethylsiloxy)methylsilane;

PDMS macromonomers, such as polydimethylsiloxanes containing monoacryloyloxy or monomethacryloyloxy end groups, for example, those having the following formula:

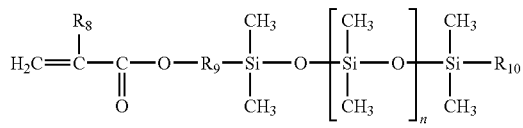

in which:

$R_8$ is a hydrogen atom or a methyl group; such as methyl;

$R_9$ is a linear or branched, such as linear, divalent hydrocarbon-based group containing from 1 to 10 carbon atoms and optionally containing one or two ether bonds —O—; such as ethylene, propylene or butylene;

$R_{10}$ is a linear or branched alkyl group containing from 1 to 10 carbon atoms, for example from 2 to 8 carbon atoms; such as methyl, ethyl, propyl, butyl or pentyl;

n is an integer ranging from 1 to 300, for instance ranging from 3 to 200 and further for example ranging from 5 to 100.

Monomethacryloyloxypropylpolydimethylsiloxanes such as those sold under the name PS560-K6 by UCT (United Chemical Technologies Inc.) or under the name MCR-M17 by Gelest Inc. may be used in at least one embodiment.

In at least one embodiment, the soluble monomers may be chosen from (meth)acryloxypropyltris(trimethylsiloxy)silane, (meth)acryloxypropylbis(trimethylsiloxy)methylsilane, (meth)acryloxymethyltris(trimethylsiloxy)silane, (meth)acryloxymethylbis(trimethylsiloxy)methylsilane and monomethacryloyloxypropylpolydimethylsiloxanes; and mixtures thereof.

An insoluble monomer that may be used, non-limiting mention may be made, alone or as a mixture, of the following monomers, and also the salts and mixtures thereof;

(i) the (meth)acrylates of formula: $CH_2=C(CH_3)$—$COOR_1$ or $CH_2=CH$—$COOR_1$ in which $R_1$ represents a group chosen from:

a linear or branched alkyl group containing from 1 to 30 carbon atoms, the alkyl group possibly comprising in its chain at least one hetero atom chosen from O, N and S; and/or possibly comprising at least one substituent chosen from —OH, halogen atoms (F, Cl, Br or I) and —NR'R" with R' and R", which may be identical or different, chosen from linear or branched $C_1$-$C_4$ alkyls; and/or possibly being substituted with at least one polyoxyalkylene group, such as with a $C_2$-$C_4$ alkylene, such as a polyoxyethylene and/or a polyoxypropylene, the polyoxyalkylene group comprising a repetition of from 5 to 30 oxyalkylene units;

a cyclic alkyl group containing from 3 to 30 carbon atoms, the cyclic alkyl group possibly comprising in its chain at least one hetero atom chosen from O, N and S and/or possibly comprising at least one substituent chosen from OH and halogen atoms (F, Cl, Br or I).

Examples of $R_1$ include but are not limited to methyl, ethyl, propyl, butyl, tert-butyl, isobutyl, lauryl, stearyl, behenyl, 2-ethylhexyl, methoxyethyl, ethoxyethyl, methoxypolyoxyethylene 30, trifluoroethyl, 2-hydroxyethyl, 2-hydroxypropyl, dimethylaminoethyl, diethylaminoethyl, dimethylaminopropyl and isobornyl groups;

(ii) the (meth)acrylamides of formula: $CH_2=C(CH_3)$—$CONR_3R_4$ or $CH_2=CH$—$CONR_3R_4$, in which:

$R_3$ and $R_4$, which may be identical or different, are independently chosen from a hydrogen atom and linear or branched alkyl groups comprising from 1 to 12 carbon atoms, possibly comprising at least one substituent chosen from —OH, halogen atoms (F, Cl, Br or I) and —NR'R" with R' and R", which may be identical or different, chosen from linear or branched $C_1$-$C_4$ alkyls; or $R_3$ represents a hydrogen atom and $R_4$ represents a 1,1-dimethyl-3-oxobutyl group.

As examples of alkyl groups that can be used as $R_3$ and $R_4$, mention may be made of n-butyl, t-butyl, n-propyl, isooctyl, isononyl, undecyl, dimethylaminoethyl, diethylaminoethyl and dimethylaminopropyl;

(iii) ethylenically unsaturated monomer(s) comprising at least one carboxylic, phosphoric or sulfonic acid function, such as crotonic acid, maleic anhydride, itaconic acid, fumaric acid, maleic acid, styrenesulfonic acid, vinylbenzoic acid, vinylphosphoric acid, acrylic acid, methacrylic acid and acrylamidopropanesulfonic acid, and salts thereof;

(iv) the vinyl esters of formula: $R_6$—$COO$—$CH=CH_2$ in which $R_6$ represents a linear or branched alkyl group containing from 1 to 22 carbon atoms or a cyclic alkyl group containing from 3 to 6 carbon atoms and/or an aromatic group, for example of benzene, anthracene or naphthalene type;

(v) ethylenically unsaturated monomers comprising at least one tertiary amine function, such as 2-vinylpyridine or 4-vinylpyridine, and mixtures thereof;

(vi) styrene and derivatives thereof;

(vii) oligopeptides functionalized with a (meth)acrylate function;

(viii) the ethers of vinyl alcohol and of an alcohol of formula $R_6O-CH=CH_2$ in which $R_6$ represents a linear or branched alkyl group containing from 1 to 22 carbon atoms;

(ix) ethylenic monomers in which the ester group contains silanes or siloxanes, and which contain only one silicon atom, such as (meth)acryloxypropyltrimethoxysilane;

(x) carbon-based macromonomers with a polymerizable end group. The term "macromonomer with a polymerizable end group" means any oligomer comprising on only one of its ends a polymerizable end group capable of reacting during the polymerization reaction with ethylenic monomers. The polymerizable group of the macromonomer may be an ethylenically unsaturated group capable of undergoing free-radical polymerization. The polymerizable end group may be, for example, a vinyl or (meth)acrylate (or (meth)acryloxy) group and, in at least one embodiment, a (meth)acrylate group. The term "carbon-based macromonomer" means a non-silicone macromonomer, such as an oligomeric macromonomer obtained by polymerization of non-silicone ethylenically unsaturated monomer(s), and mainly by polymerization of acrylic monomers and/or non-acrylic vinyl monomers.

As carbon-based macromonomers with a polymerizable end group, non-limiting mention may be made, for example, of:

(a) linear or branched $C_6$-$C_{22}$, such as $C_8$-$C_{18}$, alkyl (meth)acrylate homopolymers and copolymers, containing a polymerizable end group chosen from vinyl or (meth)acrylate groups, among which mention may be made, for example, of: poly(2-ethylhexyl acrylate) macromonomers containing mono(meth)acrylate end groups; polyldodecyl acrylate) or poly(dodecyl methacrylate) macromonomers containing mono(meth)acrylate end groups; poly(stearyl acrylate) or poly(stearyl methacrylate) macromonomers containing mono(meth)acrylate end groups.

Such macromonomers are described in European Patent Nos. EP 895 467 and EP 96459 and in the article Gillman, Polymer Letters, Vol. 5, page 477-481 (1967).

Mention may be made, for example, of macromonomers based on poly(2-ethylhexyl acrylate) or poly(dodecyl acrylate) containing mono(meth)acrylate end groups.

(b) polyolefins with an ethylenically unsaturated end group, such as those with a (meth)acrylate end group. Examples of such polyolefins that may be mentioned, for example, include the following macromonomers, it being understood that they contain a (meth)acrylate end group: polyethylene macromonomers, polypropylene macromonomers, macromonomers of polyethylene/polypropylene copolymer, macromonomers of polyethylene/polybutylene copolymer, polyisobutylene macromonomers; polybutadiene macromonomers; polyisoprene macromonomers; polybutadiene macromonomers; poly(ethylene/butylene)-polyisoprene macromonomers.

Such macromonomers are described, for example, in European Patent No. EP 1 347 013 or in U.S. Pat. No. 5,625,005, which mentions ethylene/butylene and ethylene/propylene macromonomers containing a (meth)acrylate reactive end group. Mention may also be made of poly(ethylene/butylene) methacrylate, such as the product sold under the name Kraton Liquid L-1253 by Kraton Polymers.

(xi) the di-n-alkylitaconates of formula $CH_2=C(CH_2-COO(CH_2)_{n-1}-CH_3)-COO(CH_2)_{n-1}-CH_3$, with n being an integer greater than or equal to 1, such as an integer ranging from 1 to 12.

Among the salts, mention may be made of those obtained by neutralization of acidic groups using mineral bases such as sodium hydroxide, potassium hydroxide or ammonium hydroxide, or organic bases such as alkanolamines, for instance monoethanolamine, diethanolamine, triethanolamine or 2-methyl-2-amino-1-propanol.

Mention may also be made of the salts formed by neutralization of the tertiary amine units, for example using a mineral or organic acid. Among the mineral acids that may be mentioned are sulfuric acid, hydrochloric acid, hydrobromic acid, hydriodic acid, phosphoric acid and boric acid. Among the organic acids that may be mentioned are acids comprising at least one group chosen from carboxylic, sulfonic and phosphonic groups. These acids may be linear, branched or cyclic aliphatic acids or alternatively aromatic acids. Further, these acids may also comprise at least one hetero atom chosen from O and N, for example in the form of hydroxyl groups. Mention may be made, for instance, of acetic acid, propionic acid and terephthalic acid, and also citric acid and tartaric acid.

In at least one embodiment, insoluble monomers that may be mentioned, alone or as a mixture, include:

(meth)acrylates, such as methyl, ethyl, propyl, butyl, isopropyl, tert-butyl or isobutyl (meth)acrylate; methoxyethyl or ethoxyethyl (meth)acrylate; trifluoroethyl methacrylate; dimethylaminoethyl methacrylate, diethylaminoethyl methacrylate; 2-hydroxypropyl methacrylate, 2-hydroxyethyl methacrylate, 2-hydroxypropyl acrylate or 2-hydroxyethyl acrylate; 2-ethylhexyl (meth)acrylate, isobornyl (meth)acrylate, lauryl (meth)acrylate, stearyl (meth)acrylate or behenyl (meth)acrylate, and also the salts thereof;

ethylenically unsaturated monomers comprising at least one carboxylic acid function, such as (meth)acrylic acid and salts thereof; or maleic anhydride.

In at least one embodiment, the insoluble monomers may be chosen from methyl or ethyl (meth)acrylate, (meth)acrylic acid and maleic anhydride.

The polymer particle dispersion according to the present disclosure also comprises a liquid silicone medium in which the particles are dispersed.

The term "liquid medium" as used herein means a medium having a viscosity of less than or equal to 7000 centipoises at 20° C.

According to the present disclosure, the medium may be a silicone medium if it comprises at least 50% by weight, for example from 50.1% to 100% by weight, such as from 60% to 99% by weight or further from 65% to 95% by weight, or even further still from 70% to 90% by weight, relative to the total weight of the silicone medium, of silicone compound that is liquid at 25° C., having a global solubility parameter according to the Hansen solubility space of less than or equal to 20 $(MPa)^{1/2}$, or a mixture of such compounds.

The global solubility parameter δ according to the Hansen solubility space is defined in the article "Solubility parameter values" by Grulke, in the book "Polymer Handbook" 3rd Edition, Chapter VII, pages 519-559, by the relationship:

$$\delta=(d_D^2+d_P^2+d_H^2)^{1/2}$$

in which:

$d_D$ characterizes the London dispersion forces derived from the formation of dipoles induced during molecular impacts, $d_P$ characterizes the Debye interaction forces between permanent dipoles, $d_H$ characterizes the specific interaction forces (such as hydrogen bonding, acid/base bonding, donor/acceptor bonding, etc.).

The definition of solvents in the three-dimensional solubility space according to Hansen is described in Hansen's article: "The three dimensional solubility parameters," J. Paint Technol. 39, 105 (1967).

Among the liquid silicone compounds with a global solubility parameter according to the Hansen solubility space of less than or equal to 20 $(MPa)^{1/2}$, mention may be made of volatile or non-volatile silicone oils, alone or as a mixture.

The term "volatile oil" as used herein means an oil capable of evaporating from the skin or the lips in less than one hour, such as an oil having a vapor pressure, at room temperature and atmospheric pressure, ranging from $10^{-3}$ to 300 mmHg (0.13 Pa to 40 000 Pa).

The non-volatile silicone oils that may be mentioned include but are not limited to:

non-volatile polydialkylsiloxanes, such as non-volatile polydimethylsiloxanes (PDMS), optionally substituted with aliphatic and/or aromatic groups, which may be fluorinated, and/or comprising functional groups such as hydroxyl, thiol and/or amine groups; such as polysiloxanes modified with fatty acids (e.g., of $C_8$-$C_{20}$), fatty alcohols (e.g., of $C_8$-$C_{20}$) or polyoxyalkylenes (e.g., polyoxyethylene and/or polyoxypropylene); amino polysiloxanes; polysiloxanes containing hydroxyl groups; fluorinated polysiloxanes comprising a fluoro group that is pendent or at the end of a silicone chain containing from 1 to 12 carbon atoms, all or some of the hydrogens of which are replaced with fluorine atoms;

polydimethylsiloxanes comprising alkyl, alkoxy or phenyl groups that are pendent or at the end of a silicone chain, these groups possibly containing from 2 to 24 carbon atoms;

phenyl silicones, for instance phenyl trimethicones, phenyl dimethicones, phenyl trimethylsiloxy diphenylsiloxanes, diphenyl dimethicones, diphenyl methyldiphenyl trisiloxanes; and also polymethylphenylsiloxanes, optionally substituted with aliphatic and/or aromatic groups, which may be fluorinated, and/or comprising functional groups such as hydroxyl, thiol and/or amine groups;

mixtures thereof.

Among the volatile silicone oils that may be mentioned are cyclic or linear silicone oils, containing 2 to 7 silicon atoms, and optionally comprising alkyl or alkoxy groups containing from 1 to 10 carbon atoms, such as cyclodimethylsiloxanes, cyclophenylmethylsiloxanes and linear dimethylsiloxanes, such as linear dodecamethylpentasiloxane (L5), octamethylcyclotetrasiloxane (D4), decamethylcyclopentasiloxane (D5), dodecamethylcyclohexasiloxane (D6), heptamethylhexyltrisiloxane, heptamethyloctyltrisiloxane, octamethyltrisiloxane and decamethyltetrasiloxane, and mixtures thereof.

In at least one embodiment, the dispersion comprises in the silicone medium at least one silicone compound chosen, alone or as a mixture, from:

phenyl silicones such as phenyl trimethicones, phenyl dimethicones and polymethylphenylsiloxanes;

cyclic or linear volatile silicone oils containing 2 to 7 silicon atoms, such as linear dodecamethylpentasiloxane (L5), octamethylcyclotetrasiloxane (D4), decamethylcyclopentasiloxane (D5) and dodecamethylcyclohexasiloxane (D6), and mixtures thereof.

A dispersion comprising polymer particles in a silicone medium is novel and, as such, constitutes a subject of the present disclosure.

The silicone medium may optionally comprise additional liquid compounds that may be present in an amount of strictly less than 50% by weight, such as from 1% to 40% by weight, further such as from 5% to 35% by weight, and for example ranging from 10% to 30% by weight, relative to the total weight of the silicone medium, and chosen, alone or as a mixture, from:

plant oils formed by fatty acid esters of polyols, for instance triglycerides, such as sunflower oil, sesame seed oil, rapeseed oil, macadamia oil, soybean oil, sweet almond oil, beauty-leaf oil, palm oil, grape seed oil, corn oil, arara oil, cottonseed oil, apricot oil, avocado oil, jojoba oil, olive oil and cereal germ oil;

linear, branched or cyclic esters, containing 2 to 30 carbon atoms; for instance isononyl isononanoate such as the esters of formula RCOOR' in which R represents a higher fatty acid residue containing from 7 to 19 carbon atoms and R' represents a hydrocarbon-based chain containing from 3 to 20 carbon atoms, such as palmitates, adipates, myristates and benzoates, for example diisopropyl adipate and isopropyl myristate;

hydrocarbons, for example, volatile or non-volatile, linear, branched and/or cyclic alkanes, such as optionally volatile $C_5$-$C_{60}$ isoparaffins such as isododecane, Parleam (hydrogenated polyisobutene), isohexadecane, cyclohexane, and "Isopar" products; or alternatively liquid paraffin, liquid petroleum jelly and hydrogenated polyisobutylene;

ethers containing 2 to 30 carbon atoms;

ketones containing 2 to 30 carbon atoms;

aliphatic monoalcohols, such as fatty aliphatic monoalcohols, containing 1 to 30 carbon atoms, the hydrocarbon-based chain not comprising any substitution groups, such as oleyl alcohol, decanol, dodecanol, octadecanol, octyldodecanol and linoleyl alcohol;

polyols, e.g., those containing 6 to 30 carbon atoms, such as hexylene glycol;

mixtures thereof.

In at least one embodiment, the additional liquid compounds, when they are present, are chosen, alone or as a mixture, from:

linear, branched or cyclic esters containing 2 to 30 carbon atoms; such as isononyl isononanoate, diisopropyl adipate and isopropyl myristate;

linear, branched and/or cyclic, volatile or non-volatile alkanes, such as optionally volatile $C_5$-$C_{60}$ isoparaffins such as isododecane, Parleam (hydrogenated polyisobutene), isohexadecane, cyclohexane or the "Isopar" products; or alternatively liquid paraffin, liquid petroleum jelly or hydrogenated polyisobutylene;

aliphatic fatty monoalcohols containing 8 to 30 carbon atoms, the hydrocarbon-based chain not comprising any substitution groups, such as oleyl alcohol, decanol, dodecanol, octadecanol, octyidodecanol and linoleyl alcohol.

However, according to at least one embodiment of the present disclosure, the silicone medium does not contain any additional liquid compounds.

The choice of the silicone medium may be readily made by a person skilled in the art as a function of the nature of the monomers constituting the polymer and/or of the intended use of the composition.

Among the dispersions of diblock polymers useful herein, non-limiting mention may be made of dispersions of particles of:

poly(methacryloxypropyltris(trimethylsiloxy)silane)-b-poly(methyl acrylate), poly(methacryloxypropyltris(trimethylsiloxy)silane)-b-poly(methyl acrylate-co-acrylic acid), poly(methacryloxypropyltris(trimethylsiloxy)silane-co-acrylic acid)-b-poly(methyl acrylate), poly(acryloxypropyltris(trimethylsiloxy)silane)-b-poly(methyl acrylate), poly(acryloxypropyltris(trimethylsiloxy)silane)-b-poly(methyl acrylate-co-acrylic acid), poly(acryloxypropyltris(trimethylsiloxy)silane-co-acrylic acid)-b-poly(methyl acrylate), poly(methacryloxypropylbis(trimethylsiloxy)methylsilane)-b-poly(methyl acrylate),
poly(methacryloxypropylbis(trimethylsiloxy)methylsilane)-b-poly(methyl acrylate-co-acrylic acid),
poly(methacryloxypropylbis(trimethylsiloxy)methylsilane-co-acrylic acid)-b-poly(methyl acrylate),
poly(acryloxypropylbis(trimethylsiloxy)methylsilane)-b-poly(methyl acrylate),
poly(acryloxypropylbis(trimethylsiloxy)methylsilane)-b-poly(methyl acrylate-co-acrylic acid),
poly(acryloxypropylbis(trimethylsiloxy)methylsilane-co-acrylic acid)-b-poly(methyl acrylate),
poly(polydimethylsiloxanemethacryloyloxy)-b-poly(methyl acrylate),
poly(polydimethylsiloxanemethacryloyloxy)-b-poly(methyl acrylate-co-acrylic acid),
poly(polydimethylsiloxanemethacryloyloxy-co-acrylic acid)-b-poly(methyl acrylate),
poly(polydimethylsiloxanemethacryloyloxy-co-methacryloxypropyltris(trimethylsiloxy)silane)-b-poly(methyl acrylate),
poly(polydimethylsiloxanemethacryloyloxy-co-methacryloxypropyltris(trimethylsiloxy)silane)-b-poly(methyl acrylate-co-acrylic acid),
poly(polydimethylsiloxanemethacryloyloxy-co-methacryloxypropyltris(trimethylsiloxy)silane-co-acrylic acid)-b-polymethyl acrylate),
poly(polydimethylsiloxanemethacryloyloxy-co-acryloxypropyltris(trimethylsiloxy)silane)-b-poly(methyl acrylate)
poly(polydimethylsiloxanemethacryloyloxy-co-acryloxypropyltris(trimethylsiloxy)silane)-b-poly(methyl acrylate-co-acrylic acid),
poly(polydimethylsiloxanemethacryloyloxy-co-acryloxypropyltris(trimethylsiloxy)silane-co-acrylic acid)-b-poly(methyl acrylate),
poly(methacryloxypropylbis(trimethylsiloxy)methylsilane-co-methacryloxypropyltris(trimethylsiloxy)silane)-b-poly(methyl acrylate),
poly(methacryloxypropylbis(trimethylsiloxy)methylsilane-co-methacryloxypropyltris(trimethylsiloxy)silane)-b-poly(methyl acrylate-co-acrylic acid),
poly(methacryloxypropylbis(trimethylsiloxy)methylsilane-co-methacryloxypropyltris(trimethylsiloxy)silane-co-acrylic acid)-b-poly(methyl acrylate),
poly(methacryloxypropylbis(trimethylsiloxy)methylsilane-co-acryloxypropyltris(trimethylsiloxy)silane)-b-poly(methyl acrylate),
poly(methacryloxypropylbis(trimethylsiloxy)methylsilane-co-acryloxypropyltris(trimethylsiloxy)silane-b-poly(methyl acrylate-co-acrylic acid),
poly(methacryloxypropylbis(trimethylsiloxy)methylsilane-co-acryloxypropyltris(trimethylsiloxy)silane-co-acrylic acid)-b-poly(methyl acrylate),
poly(methacryloxypropyltris(trimethylsiloxy)silane-co-acryloxypropyltris(trimethylsiloxy)silane)-b-poly(methyl acrylate),
poly(methacryloxypropyltris(trimethylsiloxy)silane-co-acryloxypropyltris(trimethylsiloxy)silane)-b-poly(methyl acrylate-co-acrylic acid),
poly(methacryloxypropyltris(trimethylsiloxy)silane-co-acryloxypropyltris(trimethylsiloxy)silane-co-acrylic acid)-b-poly(methyl acrylate),
poly(polydimethylsiloxanemethacryloyloxy-co-methacryloxypropylbis(trimethylsiloxy)methylsilane)-b-poly(methyl acrylate),
poly(polydimethylsiloxanemethacryloyloxy-co-methacryloxypropylbis(trimethylsiloxy)methylsilane)-b-polymethyl acrylate-co-acrylic acid),
poly(polydimethylsiloxanemethacryloyloxy-co-methacryloxypropylbis(trimethylsiloxy)methylsilane-co-acrylic acid)-b-poly(methyl acrylate);
poly(polydimethylsiloxanemethacryloyloxy-co-acryloxypropylbis(trimethylsiloxy)methylsilane)-b-poly(methyl acrylate),
poly(polydimethylsiloxanemethacryloyloxy-co-acryloxypropylbis(trimethylsiloxy)methylsilane)-b-poly(methyl acrylate-co-acrylic acid),
poly(polydimethylsiloxanemethacryloyloxy-co-acryloxypropylbis(trimethylsiloxy)methylsilane-co-acrylic acid)-b-poly(methyl acrylate);

in a silicone medium as defined above, such as in a phenyl silicone and/or a volatile silicone oil, for instance in a cyclic volatile silicone oil such as D5.

Among the dispersions of triblock polymers useful herein, mention may be made of dispersions of particles of:
poly(methacryloxypropyltris(trimethylsiloxy)silane)-b-poly(methyl acrylate)-b-poly(methacryloxypropyltris(trimethylsiloxy)silane,
poly(methacryloxypropyltris(trimethylsiloxy)silane-co-acrylic acid)-b-poly(methyl acrylate)-b-poly(methacryloxypropyltris(trimethylsiloxy)silane-co-acrylic acid),
poly(methacryloxypropyltris(trimethylsiloxy)silane)-b-poly(methyl acrylate-co-acrylic acid)-b-poly(methacryloxypropyltris(trimethylsiloxy)silane),
poly(acryloxypropyltris(trimethylsiloxy)silane)-b-poly(methyl acrylate)-b-poly(acryloxypropyltris(trimethylsiloxy)silane),
poly(acryloxypropyltris(trimethylsiloxy)silane-co-acrylic acid)-b-poly(methyl acrylate)-b-poly(acryloxypropyltris(trimethylsiloxy)silane-co-acrylic acid),
poly(acryloxypropyltris(trimethylsiloxy)silane)-b-poly(methyl acrylate-co-acrylic acid)-b-poly(acryloxypropyltris(trimethylsiloxy)silane),
poly(methacryloxypropylbis(trimethylsiloxy)methylsilane)-b-poly(methyl acrylate)-b-poly(methacryloxypropylbis(trimethylsiloxy)methylsilane),
poly(methacryloxypropylbis(trimethylsiloxy)methylsilane-co-acrylic acid)-b-poly(methyl acrylate)-b-poly(methacryloxypropylbis(trimethylsiloxy)methylsilane-co-acrylic acid),
poly(methacryloxypropylbis(trimethylsiloxy)methylsilane)-b-poly(methyl acrylate-co-acrylic acid)-b-poly(methacryloxypropylbis(trimethylsiloxy)methylsilane),
poly(acryloxypropylbis(trimethylsiloxy)methylsilane)-b-poly(methyl acrylate)-b-poly(acryloxypropylbis(trimethylsiloxy)methylsilane),
poly(acryloxypropylbis(trimethylsiloxy)methylsilane-co-acrylic acid)-b-poly(methyl acrylate)-b-poly(acryloxypropylbis(trimethylsiloxy)methylsilane-co-acrylic acid),
poly(acryloxypropylbis(trimethylsiloxy)methylsilane)-b-poly(methyl acrylate-co-acrylic acid)-b-poly(acryloxypropylbis(trimethylsiloxy)methylsilane),
poly(polydimethylsiloxanemethacryloyloxy)-b-poly(methyl acrylate)-b-poly(polydimethylsiloxanemethacryloyloxy),
poly(polydimethylsiloxanemethacryloyloxy-co-acrylic acid)-b-poly(methyl acrylate)-b-poly(polydimethylsiloxanemethacryloyloxy-co-acrylic acid),
poly(polydimethylsiloxanemethacryloyloxy)-b-poly(methyl acrylate-co-acrylic acid)-b-poly(polydimethylsiloxanemethacryloyloxy), poly(polydimethylsiloxanemethacryloyloxy-co-methacryloxypropyltris(trimethylsiloxy)silane)-b-poly(methyl acrylate)-b-poly(polydimethylsiloxanemethacryloyloxy-co-methacryloxypropyltris(trimethylsiloxy)silane), poly(polydimethylsiloxanemethacryloyloxy-co-methacryloxypropyltris(trimethylsiloxy)silane-co-acrylic acid)-b-poly(methyl acrylate)-b-poly(polydimethylsiloxanemethacryloyloxy-co-methacryloxypropyltris(trimethylsiloxy)silane-co-acrylic acid), poly(polydimethylsiloxanemethacryloyloxy-co-methacryloxypropyltris(trimethylsiloxy)silane)-b-poly(methyl acrylate-co-acrylic acid)-b-poly(polydimethylsiloxanemethacryloyloxy-co-methacryloxypropyltris(trimethylsiloxy)silane), poly(polydimethylsiloxanemethacryloyloxy-co-acryloxypropyltris(trimethylsiloxy)silane)-b-poly(methyl acrylate)-b-poly(polydimethylsiloxanemethacryloyloxy-co-acryloxypropyltris(trimethylsiloxy)silane), poly(polydimethylsiloxanemethacryloyloxy-co-acryloxypropyltris(trimethylsiloxy)silane-co-acrylic acid)-b-poly(methyl acrylate)-b-poly(polydimethylsiloxanemethacryloyloxy-co-acryloxypropyltris(trimethylsiloxy)silane-co-acrylic acid), poly(polydimethylsiloxanemethacryloyloxy-co-acryloxypropyltris(trimethylsiloxy)silane)-b-poly(methyl acrylate-co-acrylic acid)-b-poly(polydimethylsiloxanemethacryloyloxy-co-acryloxypropyltris(trimethylsiloxy)silane), poly(methacryloxypropyltris(trimethylsiloxy)silane-co-acryloxypropyltris(trimethylsiloxy)silane)-b-polymethyl acrylate)-b-poly(methacryloxypropyltris(trimethylsiloxy)silane-co-acryloxypropyltris(trimethylsiloxy)silane, poly(methacryloxypropyltris(trimethylsiloxy)silane-co-acryloxypropyltris(trimethylsiloxy)silane-co-acrylic acid)-b-poly(methyl acrylate)-b-poly(methacryloxypropyltris(trimethylsiloxy)silane-co-acryloxypropyltris(trimethylsiloxy)silane-co-acrylic acid), poly(methacryloxypropyltris(trimethylsiloxy)silane-co-acryloxypropyltris(trimethylsiloxy)silane)-b-poly(methyl acrylate-co-acrylic acid)-b-poly(methacryloxypropyltris(trimethylsiloxy)silane-co-acryloxypropyltris(trimethylsiloxy)silane), in a silicone medium as defined above, for instance in a phenyl silicone and/or a volatile silicone oil, and in at least one embodiment, in a cyclic volatile silicone oil such as D5.

The dispersion according to the present disclosure for instance has a solids content ranging from 5% and 80% by weight, such as 8% to 70% by weight and further ranging from 10% to 60% by weight, for example 15% to 50% by weight and further still ranging from 18% to 25% by weight.

The polymer dispersion may be manufactured by any means known to those skilled in the art, such as by controlled free-radical polymerization or by living polymerization, for example via the nitroxide/alkoxyamine, ATRP, organocobalt, RAFT/MADIX, degenerative transfer, TERP (tellurium) or selenium techniques, via Iniferter, or via any living polymerization process (anionic or cationic), via metallocene, ROMP (ring-opening metathesis polymerization), cationic or anionic ROP (ring-opening polymerization), GTP (group-transfer polymerization), tetraphenylethane derivatives or diphenylethylene. The techniques used for the formation of each block may be identical or different.

A typical process may comprise preparing the first block, referred to as the soluble block, in the silicone dispersion medium, by polymerization of the monomer(s), a control agent and an initiator, if necessary. Next, the monomer(s) of the "insoluble" block is (are) added in the presence or absence of initiator. The reaction temperature ranges, for instance, from −30 to 200° C., such as from 0 to 160° C. and further for example from 40 to 140° C. Additional blocks may be polymerized according to the same process. For each of the blocks, the monomer(s) may be added simultaneously, in batch mode, semi-continuously or consecutively. Multiblock polymers will then be obtained.

If the first block, referred to as the soluble block, is synthesized in bulk, the "insoluble" block may then be synthesized in bulk or in solution. The solvent may be a silicone solvent as defined herein, which leads at the end of the synthesis of the copolymer to a dispersion directly in the silicone medium. The solvent used may also be a solvent common to all the blocks; for example, the subsequent addition of a silicone solvent as defined above herein and the optional removal of the common solvent will lead to the desired dispersion in the silicone medium.

If the whole copolymer is synthesized in bulk, the addition of a silicone solvent as defined above will lead to the desired dispersion.

If all the blocks are synthesized in solution, in a common solvent, the subsequent addition of a silicone solvent as defined above and the optional removal of the common solvent will lead to the desired dispersion in the silicone media. It is also possible at this stage to remove the common solvent in order to recover the polymer alone and before dispersing it in a silicone solvent as defined above, which will lead to the desired dispersion.

Finally, if all the blocks are synthesized directly in a silicone solvent as defined above, the dispersion is obtained directly, in a single step. The latter process is used in at least one embodiment.

Once the dispersion has been obtained, it is possible to change the silicone medium by removal/addition of a new silicone solvent or by addition/optional removal of the first solvent.

For instance, the first block may be prepared by controlled radical polymerization (CRP), the second block may also be prepared by CRP or by conventional polymerization.

In another embodiment, the soluble block is synthesized in bulk, and then dissolved in a silicone solvent according to the present disclosure, and then the insoluble block is synthesized in this silicone solvent; such that a dispersion of the polymer in the silicone solvent is thus directly obtained.

In at least one embodiment of the present disclosure, once the dispersion has been obtained, it is possible to add thereto one or more monomers C whose homopolymers are either of soluble type or of insoluble type, according to the definition given above, and for example insoluble, in the medium, in order to continue the polymerization on the copolymers containing blocks A-B already formed, which leads to the formation of triblock copolymers A-B-C.

The additional monomer(s) C may be present in an amount such that the total amounts of soluble and insoluble monomers remain within the total ranges mentioned above.

When the starting copolymer is a triblock copolymer of structure A-B-A, the polymerization of C may lead to a pentablock copolymer of structure C-A-B-A-C or A-B-C-B-A, depending on the polymerization technique and/or the transfer agent used.

The polymerization initiator may be any initiator known to those skilled in the art for free-radical polymerization (peroxides, azo compounds, redox couple or photochemical initiator). In the case of certain controlled radical polymerization techniques, the same compound may have the role of polymerization initiator and may be the control agent, as is the case for alkoxyamines. For non-radical polymerizations, i.e., ionic (anionic or cationic) polymerizations, a person skilled in the art can select the appropriate initiator.

During the polymerization, it is possible to crosslink the particles of the dispersion either in the core (insoluble block), or in the shell (soluble block), or in both.

For instance, the crosslinking is performed in the core of the particle so as to obtain a film-forming deposit once the solvent of the dispersion has evaporated off. Among the comonomers that may be used for the crosslinking during the polymerization and/or after the polymerization by activation, mention may be made of allyl (meth)acrylate, cinnamoyl (meth)acrylate, glycidyl (meth)acrylate, maleic anhydride, and monomers containing an isocyanate side function, which, after addition of diamine or of diol, will form a urea or urethane bond, respectively.

The crosslinking may also be obtained by post-crosslinking of the silane function Si—H or Si-alkyl by hydrolysis in protic medium; in at least one embodiment, the monomer is methacryloxypropyltrimethoxysilane.

The crosslinking during the polymerization is for instance performed by adding difunctional comonomers, for instance of allyl diacrylate, dimethacrylate or methacrylate type.

Copolymers that self-organize in dispersion in the medium under consideration are thus obtained. The copolymers may comprise a first soluble block A and at least one second, insoluble block, B, which will cause self-organization of the polymer chains so as to form particles having at the interface with the medium the blocks A and at the core of the particle the blocks B. Once the dispersion is obtained, it is possible to add dispersants or stabilizers thereto in order to modify its physicochemical properties (viscosity, Tg, etc.).

The dispersions according to the present disclosure may be used in cosmetics. Thus, they may be present in the cosmetic compositions according to the present disclosure in an amount ranging from 0.1% to 90% by weight, for instance 0.5% to 80% by weight, such as 1% to 75% by weight and further for example 5-70% by weight of dispersion relative to the total weight of the composition.

The cosmetic compositions according to the present disclosure also comprise a cosmetically acceptable medium, i.e., a medium that is compatible with keratin materials such as facial or body skin, the lips, the hair, the eyelashes, the eyebrows and the nails.

The composition may comprise a fatty phase, which may itself comprise oils and/or solvents, which may include lipophilic, and also fatty substances that are solid at room temperature, such as waxes, pasty fatty substances and gums, and mixtures thereof.

In at least one embodiment, the constituents of the fatty phase may include volatile or non-volatile oils, which may be chosen from carbon-based, hydrocarbon-based, fluorinated, optionally branched, natural or synthetic oils, alone or as a mixture. As used herein, the term "non-volatile oil" means an oil that is capable of remaining on the skin at room temperature and atmospheric pressure for at least one hour and has, for example, a non-zero vapor pressure at room temperature (25° C.) and atmospheric pressure, of less than 0.01 mmHg (1.33 Pa).

Mention may be made of non-volatile carbon-based, such as hydrocarbon-based, oils, of plant, mineral, animal or synthetic origin, such as liquid paraffin (or petroleum jelly), squalane, hydrogenated polyisobutene (Parleam), perhydrosqualene, mink oil, macadamia oil, turtle oil, soybean oil, sweet almond oil, beauty-leaf oil, palm oil, grape seed oil, sesame seed oil, corn oil, arara oil, rapeseed oil, sunflower oil, cottonseed oil, apricot oil, castor oil, avocado oil, jojoba oil, olive oil and cereal germ oil, and shea butter; linear, branched or cyclic esters containing more than 6 carbon atoms for instance 6 to 30 carbon atoms, such as lanolic acid, oleic acid, lauric acid or stearic acid esters; esters derived from long-chain acids or alcohols (i.e., containing from 6 to 20 carbon atoms), for example the esters of formula RCOOR' in which R represents a higher fatty acid residue containing from 7 to 19 carbon atoms and R' represents a hydrocarbon-based chain containing from 3 to 20 carbon atoms, such as $C_{12}$-$C_{36}$ esters such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyidecyl palmitate, 2-octyidodecyl myristate or lactate, bis(2-ethylhexyl) succinate, diisostearyl malate, and glyceryl or diglyceryl triisostearate; higher fatty acids, for example $C_{14}$-$C_{22}$, such as myristic acid, palmitic acid, stearic acid, behenic acid, oleic acid, linoleic acid, linolenic acid and isostearic acid; higher fatty alcohols, for example $C_{16}$-$C_{22}$, such as cetanol, oleyl alcohol, linoleyl alcohol, linolenyl alcohol, isostearyl alcohol and octyldodecanol; and mixtures thereof.

Mention may also be made of decanol, dodecanol, octadecanol, liquid triglycerides of fatty acids of 4 to 10 carbon atoms, for instance heptanoic or octanoic acid triglycerides, caprylic/capric acid triglycerides; linear or branched hydrocarbons, of mineral or synthetic origin, such as liquid paraffins and derivatives thereof, petroleum jelly, polydecenes and hydrogenated polyisobutene, such as Parleam; synthetic esters and ethers, such as fatty acids, for instance, Purcellin oil, isopropyl myristate, 2-ethylhexyl palmitate, 2-octyidodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters; fatty alcohols containing from 12 to 26 carbon atoms, for instance octyldodecanol, 2-butyloctanol, 2-hexyldecanol and 2-undecylpentadecanol.

Mention may also be made of ketones that are liquid at room temperature, such as methyl ethyl ketone, methyl isobutyl ketone, diisobutyl ketone, isophorone, cyclohexanone and acetone; propylene glycol ethers that are liquid at room temperature, such as propylene glycol monomethyl ether, propylene glycol monomethyl ether acetate and dipropylene glycol mono-n-butyl ether; short-chain esters (containing from 3 to 8 carbon atoms in total), such as ethyl acetate, methyl acetate, propyl acetate, n-butyl acetate and isopentyl acetate; ethers that are liquid at room temperature, such as diethyl ether, dimethyl ether and dichlorodiethyl ether; alkanes that are liquid at room temperature, such as decane, heptane, dodecane, isododecane, isohexadecane and cyclohexane; aromatic cyclic compounds that are liquid at room temperature, such as toluene and xylene; aldehydes that are liquid at room temperature, such as benzaldehyde and acetaldehyde, and mixtures thereof.

Among the volatile compounds, mention may be made of non-silicone volatile oils, such as $C_8$-$C_{16}$ isoparaffins, for instance isododecane, isodecane and isohexadecane. Mention may be made, for example, of volatile or non-volatile alkanes that are liquid at room temperature, such as decane, heptane, dodecane, isododecane, isohexadecane, cyclohexane and isodecane, and mixtures thereof.

The fatty phase may be present in an amount ranging from 0.01% to 95% by weight, for instance from 0.1% to 90% by weight, and further ranging from 10% to 85% by weight and further still for example from 30% to 80% by weight relative to the total weight of the composition.

The composition may also comprise a hydrophilic phase comprising water or a mixture of water and of hydrophilic organic solvent(s), for instance alcohols, such as linear or branched lower monoalcohols containing from 2 to 5 carbon atoms, for instance ethanol, isopropanol or n-propanol, and polyols, for instance glycerol, diglycerol, propylene glycol, sorbitol, pentylene glycol, and polyethylene glycols, or alternatively hydrophilic $C_2$ ethers and hydrophilic $C_2$-$C_4$ aldehydes. Water or the mixture of water and of hydrophilic organic solvents may be present in the composition according to the disclosure in an amount ranging from 0.1% to 80% by weight and for example from 1% to 70% by weight relative to the total weight of the composition.

The composition according to the present disclosure may also comprise waxes and/or gums. For the purposes of the present disclosure, the term "wax" means a lipophilic compound that is solid at room temperature (25° C.), with a reversible solid/liquid change of state, having a melting point of greater than or equal to 30° C., which may be up to 120° C. By bringing the wax to the liquid state (melting), it is possible to make it miscible with the oils that may be present and to form a microscopically homogeneous mixture, but on returning the temperature of the mixture to room temperature, recrystallization of the wax in the oils of the mixture is obtained. The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes and may be of plant, mineral, animal and/or synthetic origin. In at least one embodiment, the waxes have a melting point of greater than 25° C., for example greater than 45° C. As wax that may be used in the composition of the present disclosure, mention may be made of beeswax, carnauba wax and candelilla wax, paraffin, microcrystalline waxes, ceresin and ozokerite; synthetic waxes, for instance polyethylene waxes and Fischer Tropsch waxes, and silicone waxes, for instance alkyl and alkoxy dimethicones containing from 16 to 45 carbon atoms.

The gums are generally high molecular weight polydimethylsiloxanes (PDMSs), cellulose and polysaccharide gums, and the pasty substances are generally hydrocarbon-based compounds, for instance lanolins and derivatives thereof, or alternatively PDMSs.

The nature and amount of the solid substances depend on the desired mechanical properties and textures. As a guide, the composition may contain from 0.01% to 50% by weight, for example from 1% to 30% by weight of waxes relative to the total weight of the composition.

The composition according to the present disclosure may also comprise at least one dyestuff chosen from water-soluble dyes, liposoluble dyes and pulverulent dyestuffs, for instance pigments, nacres and flakes that are well known to those skilled in the art. The dyestuffs may be present in the composition in an amount ranging from 0.01% to 50% by weight and for instance from 0.01% to 30% by weight relative to the weight of the composition.

As used herein, the term "pigments" means white or colored, mineral or organic particles of any form, which are insoluble in physiological medium and are intended to color the composition. As used herein, the term "nacres" means iridescent particles of any form, such as those produced by certain molluscs in their shell or else synthesized. The pigments may be white or colored, and mineral and/or organic. Among the mineral pigments that may be mentioned are titanium dioxide, optionally surface-treated, zirconium oxide and cerium oxide, and also zinc oxide, iron oxide (black, yellow or red) and chromium oxide, manganese violet, ultramarine blue, chromium hydrate and ferric blue, and metal powders, for instance aluminium powder and copper powder. Among the organic pigments that may be mentioned are carbon black, pigments of D & C type, and lakes based on cochineal carmine or on barium, strontium, calcium or aluminium. The nacreous pigments may be chosen from white nacreous pigments such as mica coated with titanium or with bismuth oxychloride, colored nacreous pigments such as titanium mica coated with iron oxides, titanium mica coated such as those with ferric blue or with chromium oxide, titanium mica coated with an organic pigment of the abovementioned type, and also nacreous pigments based on bismuth oxychloride.

Among the water-soluble dyes that may be mentioned are the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue.

The composition according to the present disclosure may also comprise one or more fillers, for example in an amount ranging from 0.01% to 50% by weight and for instance ranging from 0.01% to 30% by weight relative to the total weight of the composition. As used herein, the term "fillers" should be understood as meaning colorless or white, mineral or synthetic particles of any form, which are insoluble in the medium of the composition irrespective of the temperature at which the composition is manufactured. These fillers serve, for example, to modify the rheology or texture of the composition. The fillers may be mineral or organic of any form, platelet-shaped, spherical or oblong, irrespective of the crystallographic form (for example lamellar, cubic, hexagonal, orthorhombic, etc.). Mention may be made of talc, mica, silica, kaolin, polyamide (Nylon®) powders (Orgasol® from Atochem), poly-β-alanine powders and polyethylene powders, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) and of acrylic acid copolymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms such as from 12 to 18 carbon atoms, for example zinc stearate, magnesium stearate, lithium stearate, zinc laurate and magnesium myristate.

The composition may also comprise an additional polymer such as a film-forming polymer. According to the present disclosure, the term "film-forming polymer" means a polymer that is capable, by itself or in the presence of an auxiliary film-forming agent, of forming a continuous film that adheres to a support such as to keratin materials. Among the film-forming polymers that may be used in the composition of the present disclosure, mention may be made of synthetic polymers, of free-radical type or of polycondensate type, polymers of natural origin, and mixtures thereof, such as acrylic polymers, polyurethanes, polyesters, polyamides, polyureas and cellulose-based polymers, for instance nitrocellulose.

The composition according to the present disclosure may also comprise ingredients commonly used in cosmetics, such as vitamins, thickeners, gelling agents, trace elements, softeners, sequestrants, fragrances, acidifying or basifying agents, preserving agents, sunscreens, surfactants, antioxidants, hair-loss counteractants, antidandruff agents, propellants and ceramides, or mixtures thereof. Needless to say, a person skilled in the art will take care to select this or these optional additional compound(s), and/or the amount thereof, such that the advantageous properties of the composition according to the present disclosure are not, or are not substantially, adversely affected by the envisaged addition.

The composition according to the disclosure may be in the form of a suspension, a dispersion, a solution, especially an organic solution, a gel, an emulsion, for instance an oil-in-water (O/W) or water-in-oil (W/O) emulsion, or a multiple emulsion (W/O/W, polyol/O/W or O/W/O emulsion), or in the form of a cream, a paste, a mousse, a dispersion of vesicles, for instance of ionic or nonionic lipids, a two-phase or multi-phase lotion, a spray, a powder or a paste, such as a soft paste (e.g., a paste with a dynamic viscosity at 25° C. of about from 0.1 to 40 Pa·s at a shear rate of 200 $s^{-1}$, after 10 minutes of measurement in cone/plate geometry). The composition may be anhydrous, for example it may be an anhydrous paste.

A person skilled in the art may select the appropriate galenical form, and also the method for preparing it, on the basis of his general knowledge, taking into account firstly the nature of the constituents used, such as their solubility in the support, and secondly the intended use of the composition.

The composition according to the present disclosure may be a makeup composition, e.g., a complexion product such as a foundation, a makeup rouge or an eyeshadow; a lip product such as a lipstick or a lipcare product; a concealer product; a blusher, a mascara or an eyeliner; an eyebrow makeup product, a lip pencil or an eye pencil; a nail product such as a nail varnish or a nailcare product; a body makeup product; a hair makeup product (for example hair mascara or hair lacquer).

The composition according to the present disclosure may be a composition for protecting or caring for the skin of the face, the neck, the hands or the body, such as an anti-wrinkle or anti-fatigue composition for making the skin look radiant, or a moisturizing or treating composition; an antisun or self-tanning composition.

The composition according to the present disclosure may also be a hair product, for example, for holding the hairstyle or for shaping the hair. The hair compositions are for instance shampoos, hair setting gels or lotions, blow-waving lotions, or fixing and styling compositions such as lacquers or sprays. The lotions may be packaged in various forms, such as in vaporizers, pump-dispenser bottles or in aerosol containers in order to apply the composition in vaporized form or in the form of a mousse. Such packaging forms are indicated, for example, when it is desired to obtain a spray or a mousse for fixing or treating the hair.

Another aspect of the present disclosure is also a cosmetic process for making up, cleansing, protecting against the sun, shaping, dyeing and caring for keratin materials, such as body or facial skin, the nails, the hair and/or the eyelashes, comprising the application to the materials of a cosmetic composition as defined above.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently contains certain errors necessarily resulting from the standard deviation found in their respective testing measurements.

The embodiments disclosed herein are illustrated in greater detail by the non-limiting examples described below.

EXAMPLES 1 AND 2

1/ Synthesis of the Soluble Block

List of Abbreviations

MeA: methyl acrylate

ASi4: 3-acryloxypropyltris(trimethylsiloxy)silane

D5: cyclopentadimethylsiloxane

MeSi4: methacryloxypropyltris(trimethylsiloxy)silane

PMeA: poly(methyl acrylate)

PASi4: poly(3-acryloxypropyltris(trimethylsiloxy)silane)

PMeSi4: poly(methacryloxypropyltris(trimethylsiloxy)silane)

The various components of the mixture (monomer, transfer agent and initiator) were placed in contact and homogenized by stirring in a 10 ml round-bottomed flask equipped with a septum. The mixture was degassed by sparging with nitrogen for 5 minutes, and the void volume of the flask was then subjected to a strong stream of nitrogen for a few seconds. The flask was then introduced into an oil bath thermostatically maintained at 80° C. It was then removed and cooled under a stream of cold water for 7 hours. The blocks obtained were precipitated twice from cold methanol and then dried under a vacuum bell jar.

| Block 1a | Monomer | Transfer agent | Initiator | Conversion | Theoretical Mn* | Exp. Mn (g/mol)/Ip |
|---|---|---|---|---|---|---|
| Nature | 3-acryloxy-propyltris-(trimethyl-siloxy)silane | DTB | T21S | | | 12 000/1.08 |
| Mass | 2 g | 21.3 mg | 8 mg | 72% | 14 400 | |

| Block 1b | Monomer | Comonomer | Transfer agent | Initiator | Theoretical Mn* | Exp. Mn (g/mol)/Ip |
|---|---|---|---|---|---|---|
| Nature | methacryloxy-propyltris-(trimethyl-siloxy)silane | Styrene | DTB | T21S | | 33 000/1.25 |
| Mass | 1.51 g | 38 mg | 15.8 mg | 6.1 mg | 20 100 | |

DTB: tert-butyl dithiobenzoate
T21S: Trigonox 21S, tert-butyl peroxy-2-ethylhexanoate
*theoretical Mn in g/mol, at the total conversion of the soluble block

2/ Synthesis of the Insoluble Block, Formation of Dispersions

The various components of the mixture (monomer, soluble block, initiator and solvent) were placed in contact and homogenized by stirring in a Rotaflo® round-bottomed flask equipped with a septum. The mixture was degassed by sparging with nitrogen for 5 minutes, and the void volume of the flask was then subjected to a strong stream of nitrogen for a few seconds. The flask was then introduced into an oil bath thermostatically maintained at 80° C. It was then removed and cooled under a stream of cold water after variable reaction times. A dispersion was thus obtained.

| Example 1 | Soluble block | Initiator | Monomer | Solvent | Time/degree of conversion | Theoretical Mn** | Exp. Mn*** (g/mol)/Ip |
|---|---|---|---|---|---|---|---|
| Nature | Block 1a | T21S | methyl acrylate | D5 | | | 3000/1.23 |
| Mass | 252 mg | 101.8 mg* | 914 mg | 3.35 g | 5 h/14% | 6200 | |

*6.5 × 10⁻² mol/L solution of T21S in MeA
**theoretical Mn of the insoluble block in g/mol, at the conversion obtained experimentally
***experimental Mn of the insoluble block in g/mol, Ip of the block copolymer

| Example 2 | Soluble Block | Initiator | Monomer | Solvent | Time | Theoretical Mn** | Exp. Mn*** (g/mol)/Ip |
|---|---|---|---|---|---|---|---|
| Nature | Block 1b | T21S | methyl acrylate | D5 | | | 7000/1.25 |
| Mass | 233 mg | 102.8 mg* | 191 mg | 1.06 g | 18 h | 42 000 | |

*2.6 × 10⁻² mol/L solution of T21S in methyl acrylate
**theoretical Mn of the insoluble block in g/mol, at total conversion
***experimental Mn of the insoluble block in g/mol, Ip of the block copolymer

EXAMPLE 3

Characterization of the Dispersions

| Example | Theoretical dry extract | Particle diameter | mass % of soluble fraction | mol % of soluble fraction |
|---|---|---|---|---|
| 1 | 30% | 18 nm | 80% | 45.7% |
| 2 | 42% | 20 nm | 82.5% | 50% |

The conversions were measured by $^1$H NMR.

The molar masses were determined by GPC in THF with linear polystyrene standards.

The mean particle diameters were measured by dynamic light scattering with a Malvern Nano-S90 machine, taking into account the refractive index and the viscosity of the solvent.

EXAMPLE 4

Mascara Composition

A mascara having the composition below was prepared:

| | |
|---|---|
| Waxes | 17 g |
| Modified hectorite (Bentone ® 38V from Elementis) | 5.3 g |
| Propylene carbonate | 1.7 g |
| Filler | 1 g |
| Pigments | 5 g |
| Polymer dispersion of Example 1 | 12 g DM* |
| Isododecane | qs 100 g |

*DM: dry matter

After application to the eyelashes, the mascara was judged very satisfactory.

EXAMPLE 5

Stick of Lipstick

The lipstick composition below was prepared:

| | |
|---|---|
| Wax | 15% |
| Polymer dispersion of Example 2 | 10% DM |
| Non-volatile carbon-based oil | 26% |
| Pigments | 8.6% |
| Isododecane | qs 100% |

The composition obtained after application to the lips had good cosmetic properties.

EXAMPLE 6

W/O Foundation

A foundation composition comprising the compounds that follow was prepared:

| Phase A | |
|---|---|
| Cetyl dimethicone copolyol (Abil EM 90 from the company Goldschmidt) | 3 g |
| Isostearyl diglyceryl succinate (Imwitor 780K from the company Condea) | 0.6 g |
| Isododecane | 18.5 g |
| Pigments (hydrophobic iron oxides and titanium oxides) | 10 g |
| Polymer dispersion of Example 1 | 8 g DM |
| Filler | 8 g |
| Fragrance | qs |
| Phase B | |
| Water | qs 100 g |
| Magnesium sulfate | 0.7 g |
| Preserving agent (methylparaben) | qs |
| Phase C | |
| Water | 2 g |
| Preserving agent (diazolinylurea) | qs |

The composition obtained had good cosmetic properties.

EXAMPLE 7

Compacted Powder

A compacted powder having the composition below was prepared:

| Composition A: | |
|---|---|
| Talc | 30 g |
| Bismuth oxychloride | 10 g |
| Zinc stearate | 4 g |
| Nylon powder | 20 g |
| Dispersion of Example 2 | 5 g |
| Composition B: | |
| Iron oxides | 2 g |
| Liquid petroleum jelly | 6 g |

The powder was obtained in the following manner: composition A was ground in a Kenwood type mill for about 5 minutes with slow stirring, composition B was added and the mixture was ground for about 2 minutes at the same speed, and then for 3 minutes at a faster speed. The preparation was then screened through a 0.16 mm screen, and the mixture was then compacted in compact cases.

A compacted powder with good cosmetic properties was obtained. The composition obtained was easy and pleasant to apply. It was observed that the film did not migrate into the fine lines of the skin, even after having been worn for several hours.

EXAMPLE 8

Face Gel

The composition below was prepared:

| | |
|---|---|
| Isopropyl palmitate | 10 g |
| Petroleum jelly (wax) | 5 g |
| Modified hectorite (clay) | 0.15 g |
| Ozokerite (wax) | 5 g |

-continued

| | |
|---|---|
| Oxyethylenated sorbitan heptaoleate (40 OE) | 5 g |
| Dispersion of Example 1 (25% DM) | 75 g |

A gel with good cosmetic properties was obtained.

EXAMPLE 9

Care Oil

The composition below was prepared:

| | |
|---|---|
| Dispersion of Example 2 (25% DM) | 70 g |
| Jojoba oil | 15 g |
| Soybean oil | 15 g |

A care oil that may be applied to the body or the face was obtained.

What is claimed is:

1. A cosmetic composition comprising, in a cosmetically acceptable medium, at least one dispersion of polymer particles in a liquid silicone medium, said polymer particles ranging from 10 to 500 nm in size, and said polymer being a copolymer comprising at least one first block that is soluble in said silicone medium and at least one second block that is insoluble in said silicone medium, wherein the copolymer comprises at least one soluble monomer chosen, alone or as a mixture, from methacryloxypropyltris-(trimethylsiloxy)silane, methacryloxypropylbis(trimethylsiloxy)methylsilane, acryloxypropylbis(trimethylsiloxy)methylsilane, methacryloxymethyltris(trimethylsiloxy)silane, acryloxymethyltris(trimethylsiloxy)silane, methacryloxymethylbis(trimethylsiloxy)-methylsilane and acryloxymethylbis(trimethylsiloxy)methylsilane.

* * * * *